US010261003B2

(12) United States Patent
Martin (10) Patent No.: US 10,261,003 B2
(45) Date of Patent: Apr. 16, 2019

(54) LOW PROFILE PANEL FOR RECORDING HAIL STRIKES ON A STRUCTURE

(71) Applicant: Hail Signature Technologies, L.L.C., Stillwell, KS (US)

(72) Inventor: Carl Edwin Martin, Independence, MO (US)

(73) Assignee: Hail Signature Technologies, L.L.C., Stilwell, KS (US)

( * ) Notice: Subject to any disclaimer, the term of this patent is extended or adjusted under 35 U.S.C. 154(b) by 347 days.

(21) Appl. No.: 15/139,051

(22) Filed: Apr. 26, 2016

(65) Prior Publication Data

US 2017/0108419 A1 Apr. 20, 2017

Related U.S. Application Data

(60) Provisional application No. 62/244,093, filed on Oct. 20, 2015.

(51) Int. Cl.
*G01N 3/30* (2006.01)
*E04D 13/00* (2006.01)
*G01W 1/14* (2006.01)

(52) U.S. Cl.
CPC ............... *G01N 3/30* (2013.01); *E04D 13/00* (2013.01); *G01W 1/14* (2013.01)

(58) Field of Classification Search
CPC . G01N 3/00; G01N 17/00; E04D 1/30; E04D 13/00; E04D 2001/308; G01L 5/0052; G01W 1/00; G01W 1/14; E04B 7/18; F24S 40/85
See application file for complete search history.

(56) References Cited

U.S. PATENT DOCUMENTS

| 6,769,287 B2 | 8/2004 | Stewart et al. |
| 7,886,574 B2 | 2/2011 | Kaneko |
| 7,945,388 B2 | 5/2011 | Housen et al. |
| 8,033,156 B2 | 10/2011 | Housen |
| 8,106,769 B1 | 1/2012 | Maroney et al. |
| 8,400,299 B1 | 3/2013 | Maroney et al. |
| 8,749,381 B1 | 6/2014 | Maroney et al. |

(Continued)

FOREIGN PATENT DOCUMENTS

EP 0222640 A2 5/1987

OTHER PUBLICATIONS

PCT International Search Report and Written Opinion from PCT Application No. PCT/US2013/023484 entitled System for Recording Information Associated With Hail Storm Event and Determining Structure Damage Based on Same (dated May 15, 2013).

(Continued)

*Primary Examiner* — Peter J Macchiarolo
*Assistant Examiner* — Nathaniel J Kolb
(74) *Attorney, Agent, or Firm* — Hovey Williams LLP (57) ABSTRACT

The roof construction broadly includes a sloped roof and a low-profile hail strike recording panel. The roof includes a plurality of shingles arranged in partially overlapped courses. The panel includes a deformable hail impact portion that is calibrated so that deformation caused by a hail strike corresponds with a known impact energy. The panel is secured to the roof so that the impact portion faces skyward in generally the same orientation as the roof. The impact portion of the panel engages and overlies at least part of one or more of the shingles.

19 Claims, 6 Drawing Sheets

(56) References Cited

U.S. PATENT DOCUMENTS

| | | |
|---|---|---|
| 2004/0112353 A1 | 6/2004 | Stewart et al. |
| 2005/0102947 A1* | 5/2005 | McCaskill .............. E04D 1/205 |
| | | 52/518 |
| 2009/0255201 A1 | 10/2009 | Kraus, Jr. et al. |
| 2009/0326822 A1 | 12/2009 | Housen et al. |
| 2009/0326835 A1 | 12/2009 | Housen |
| 2011/0241704 A1 | 10/2011 | Laflamme et al. |
| 2014/0007703 A1 | 1/2014 | Martin |
| 2014/0230574 A1 | 8/2014 | Ayon |
| 2014/0260001 A1* | 9/2014 | Kiik ........................ H02S 20/25 |
| | | 52/173.3 |
| 2015/0082883 A1* | 3/2015 | Moffatt ................. G01N 17/00 |
| | | 73/431 |

OTHER PUBLICATIONS

ASTM International, Designation: D 3746-85 (Reapproved 2002), Standard Test Method for Impact Resistance of Bituminous Roofing Systems (Copyright dated 2002).

PanelTec, Product Data Sheets (available Oct. 2012).

\* cited by examiner

LOW PROFILE PANEL FOR RECORDING HAIL STRIKES ON A STRUCTURE

CROSS REFERENCE TO RELATED APPLICATION

The present application claims priority from U.S. Provisional Application No. 62/244,093 filed Oct. 20, 2015, entitled LOW PROFILE PANEL FOR RECORDING HAIL STRIKES ON A STRUCTURE, which is hereby incorporated in its entirety by reference herein.

BACKGROUND

1. Field

The present invention relates generally to measurement and recording of structural damage data. More specifically, embodiments of the present invention concern a recording device for use as part of a roof construction to record hail strike data associated with one or more hail strikes and to use the recorded data to determine damage to the roof.

2. Discussion of Prior Art

Those ordinarily skilled in the insurance and construction industries will understand that hail storms are able to inflict significant damage to roofs and other building features. Hail damage evaluation is typically based upon eye witness reports, post-storm examination of building materials including a visual comparative analysis of damaged and undamaged roof materials, identification and examination of damage to other adjacent building features, and analysis of recorded weather data. The threshold for damage sufficient to require roof replacement is typically determined by testing a sample of roof material.

However, conventional methods of determining the amount of damage to a particular roof are deficient for various reasons. For instance, the above methods involve analysis that is often highly subjective, such as visual inspection of the roof material and surrounding building components.

There has been at least one attempt to accurately record the impact energy experienced by a roof during a hail storm event. This system is disclosed in U.S. Pat. No. 9,121,779 entitled SYSTEM FOR RECORDING INFORMATION ASSOCIATED WITH HAIL STORM EVENT AND DETERMINING STRUCTURE DAMAGE BASED ON SAME, assigned of record to the assignee of the present application, the entirety of which is incorporated by reference herein.

SUMMARY

The following brief summary is provided to indicate the nature of the subject matter disclosed herein. While certain aspects of the present invention are described below, the summary is not intended to limit the scope of the present invention.

Embodiments of the present invention provide a hail strike recording device that does not suffer from the problems and limitations of the prior art.

One aspect of the present invention concerns a roof construction. The roof construction broadly includes a sloped roof and a low-profile hail strike recording panel. The roof includes a plurality of shingles arranged in partially overlapped courses. The low-profile hail strike recording panel includes a deformable hail impact portion that is calibrated so that deformation caused by a hail strike corresponds with a known impact energy. The panel is secured to the roof so that the impact portion faces skyward in generally the same orientation as the roof. The impact portion of the panel engages and overlies at least part of one or more of the shingles.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Preferred embodiments of the invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION

Figure 1:
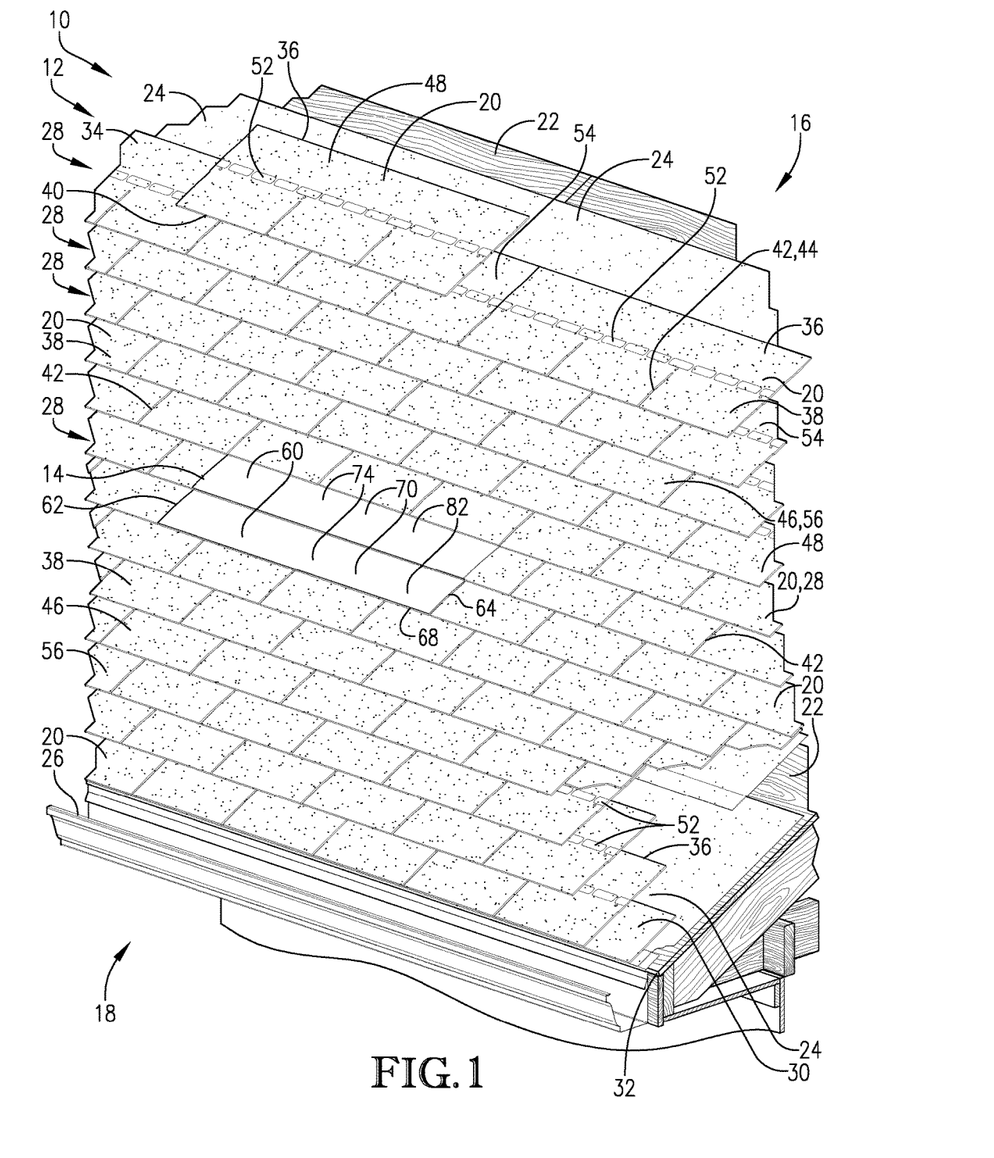
FIG. 1 is a fragmentary, partially sectioned perspective view of a roof construction in accordance with one embodiment of the present invention, with the roof construction including a roof and a hail strike recording device.

Turning initially to FIG. 1, a roof construction 10 is shown in accordance with a preferred embodiment of the present invention to record information about one or more hail strikes, thereby facilitating evaluation of any roof damage caused by the hail strikes. It will be appreciated that hail stones can vary significantly in size and mass. For instance, hail stone diameter can range from pea-size to softball-size. Generally, pea-size or smaller hail causes very little to no damage to most conventional shingled roofs. Thus, the present invention is generally not needed to sense such small hail stones. Also, because baseball-size and softball-size hail generally cause significant roof damage, the present invention is not needed to sense these very large hail stones. However, it has been found that the present invention is very effective for sensing the presence of hail stone sizes that range between these very small and very large hail stone sizes.

The roof construction 10 preferably includes a sloped shingled roof 12 and a hail strike recording device 14. The roof 12 presents a relatively higher end 16 and a relatively lower end 18. The roof 12 generally includes a plurality of shingles 20 and a roof deck 22 covered with a roof underlayment 24. The roof deck 22 is preferably supported on a building framework (not shown), such as trusses, beams, and/or arches.

It will be appreciated that the illustrated roof construction 10 could have an alternative construction without departing from the spirit of the present invention. For example, the illustrated sloped roof 12 could be variously sized and shaped, and could be pitched at various angles other than that shown in the drawing figures or entirely vertical or horizontal. Further, the depicted roof construction 10 may include multiple roof sections instead of the single roof section 12 shown in the drawing figures. As will be discussed, one or more recording devices can be selectively positioned along the roof to provide optimal sensing of the hail storm event. For instance, one or more recording devices 14 can be positioned to avoid event sensing interference by exposed elements (not shown) such as chimneys and vents. Additionally, the size of the roof will often impact the number of recording panels installed. As will be discussed in greater detail below, generally, the surface area of the roof will be proportional to the number of recording panels (more specifically, the surface area presented by the recording panels) installed.

The roof deck 22 is formed from continuous or closely spaced wood plank decking (or wood decking). Suitable decking materials are generally well known and may include plywood and/or oriented strand board (OSB). Preferably, the material used for the roof deck 22 will be compliant with the standards set by ASTM International (also known as the American Society for Testing and Materials) and/or the building codes and standards of the particular jurisdiction wherein the roof construction is located.

The roof underlayment 24 is interposed between the roof deck 22 and the shingles 20. Suitable underlayment materials are generally well known. Asphalt saturated, non-perforated organic felt underlayments are among the most common underlayments used for roof constructions including asphalt shingles. Other underlayment materials are equally suitable for the present invention, including, but not limited to, polymer-modified bitumen, rubberized asphalt, and/or non-bitumen synthetic. The arrangement of the underlayment may vary depending on the slope of the roof, the local climate (weather conditions), and other factors. Preferably, the material used for the roof underlayment and the arrangement thereof on the roof will be compliant with standards set by ASTM International and/or the building codes and standards of the particular jurisdiction wherein the roof construction is located.

Roof constructions generally include flashing (not shown). Flashing is often necessary around the perimeter of the roof, around roof penetrations (such as plumbing stacks and vents), on open valleys, and around vertical surfaces. Whether or not flashing will be necessary for a particular roof construction depends on a number of factors. Preferably, the type of flashing and the arrangement thereof on the roof will be compliant with standards set by ASTM International and/or the building codes and standards of the particular jurisdiction wherein the roof construction is located.

The roof construction 10 of the illustrated embodiment also includes a gutter 26 configured to collect water draining off the lower end 18 of the roof 12 and direct it away from the roof 12 and the underlying building (not shown). The present invention is not limited to any particular type of gutter system, and in some aspects of the present invention a gutter may not be necessary. Preferably, the dimensions and arrangement of the gutter system will conform to the building codes and standards of the particular jurisdiction wherein the roof construction is located.

In the illustrated embodiment, the shingles 20 are arranged in adjacent, overlapped courses or rows 28 on the roof 12. Generally, a starter course 30 is attached along the lowermost horizontal edge 32 of the sloped roof section 12. Additional courses 28 of shingles 20 progress upwardly toward the higher end 16 of the roof 12 in overlapping relation culminating along the ridge portion (not shown).

The shingles 20 depicted in the illustrated embodiment are standard three-tab asphalt roof shingles (also known as strip shingles). The standard shingles 20 have a substantially rectangular shape presenting a rectangular length dimension of thirty-six (36) inches and a rectangular width dimension of twelve (12) inches. Generally, asphalt shingles are made of a base material, a filler material, and a surfacing material. The base material is typically comprised of organic felt or glass-fiber mat, which supports and strengthens the shingle. The filler material is typically made of various asphalt compositions. The surfacing material is generally in the form of mineral granules, which provides a protective barrier from exposure to the surrounding climate and improves fire resistance. Additional information pertaining to asphalt shingles can be obtained from ASTM International.

Each of the shingles 20 (to the exception of shingles in optionally modified courses, such as the starter course 30) present an upper shingle section 34 extending from an upper end 36 and a lower shingle section 38 extending from the upper section 34 to a lower end 40 (or butt end). The lower section 38 includes slots 42 extending from the lower end 40 toward the upper shingle section 34 to a slot terminus 44. For each shingle 20, the slots 42 preferably form three (3) individual rectangular tabs 46 having a rectangular length of approximately twelve (12) inches and a rectangular width of approximately five (5) inches. The upper and lower sections 34 and 38 of each shingle 20 cooperatively present a top surface 48 and a bottom surface 50. Extending longitudinally along the top surface 48 is an adhesive bead or strip 52, which is preferably positioned above the slot termini 44 along the upper section 34. Generally, the adhesive strip 52 is applied to the shingles 20 by the shingle manufacturer and contains a means for thermal activation; however, the adhesive strip 52 may be applied to the shingles 20 upon installation without departing from the spirit of the present invention. The adhesive bead 52 is shown as spaced apart segments (see FIG. 3); however, the depicted arrangement of the adhesive bead 52 does not limit the spirit of the present invention. The adhesive bead 52 is preferably positioned to contact the bottom surface 50 of the adjacent overlapping (i.e., upper) shingle 20. The shingles comprising the starter course 30 and the termination course or row (not shown) are often modified upon installation and may not include the features described above.

It should be understood that the present invention is not limited to the standard size three-tab asphalt roof shingles of the illustrated embodiment. The present invention is equally applicable to roof constructions including various types of shingles made from different materials and presenting dimensions different than the shingles of the illustrated embodiment. For example, instead of standard three-tab shingles, metric shingles may be used without departing from the present invention. Metric shingles generally have a substantially rectangular shape presenting a rectangular length dimension of thirty-nine and three-eighths (39 & 3/8) inches and a rectangular width dimension of thirteen and one-fourth (13 & 1/4) inches. Importantly, it should be understood that a roof constructing having laminated shingles (also known as architectural shingles), hybrid shingles, wood shingles, metal shingles, slate shingles, and/or tile shingles are all within the ambit of the present invention. Furthermore, it should be understood that the present invention applies to shingle courses formed from a single continuous shingle or an equivalent thereto. It is most important, however, that the shingles be arranged in overlapped courses, as will be subsequently described.

As depicted in the illustrated embodiment, the shingles 20 are arranged in partially overlapped courses 28 on the sloped roof 12, such that adjacent courses present an overlapped shingle section 54 wherein the upper section(s) 34 of a subjacent one or more of the shingles 20 underlies the lower section(s) 38 of a superjacent one or more of the shingles 20. As will be described, the shingles in adjacent courses are longitudinally offset so that each superjacent shingle extends along most of the length of one of the subjacent shingles and a small part of the length of the adjacent subjacent shingle. Furthermore, (as depicted in the illustrated embodiment), the butt end 40 of the shingles 20 in the superjacent course or row 28 abuts or extends just below the slot terminus 44 of the shingles 20 in the subjacent course or row 28. Thus, when installed in consecutive overlapping rows 28, the top surface 48 of the lower shingle section 38 presents an exposed surface 56. In the illustrated embodiment, the exposed surface 56 of the shingles 20 is comprised of the tabs 46 discussed above.

Figure 3:
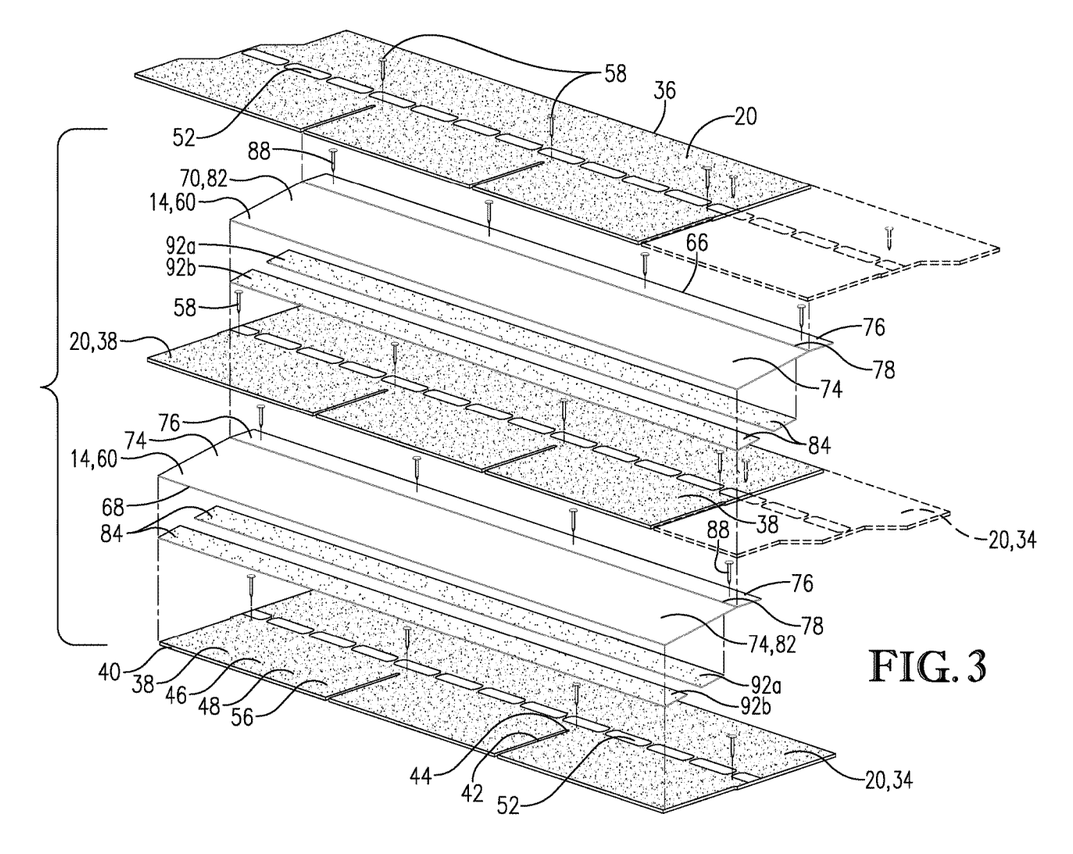
FIG. 3 is an exploded perspective view of part of the roof construction shown in FIG. 1, particularly showing the multiple panels that make up the preferred hail strike recording device and the manner in which the panels are partly overlapped with the shingles.
Figure 6:
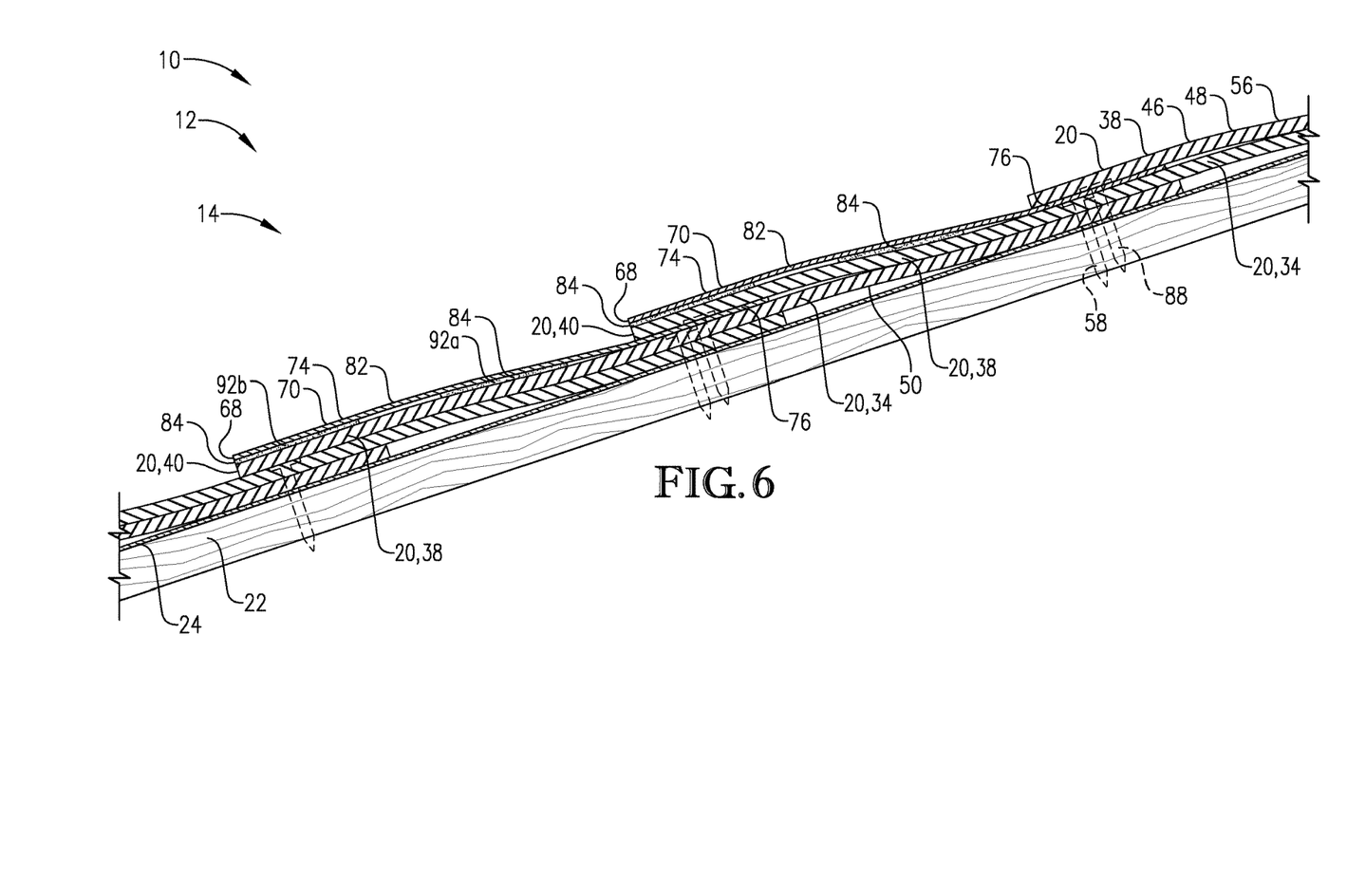
FIG. 6 is a fragmentary cross section view of the roof construction shown in FIG. 1, particularly showing the impact portion of each panel engaging and overlying the corresponding shingles.
Figures 7, 8:
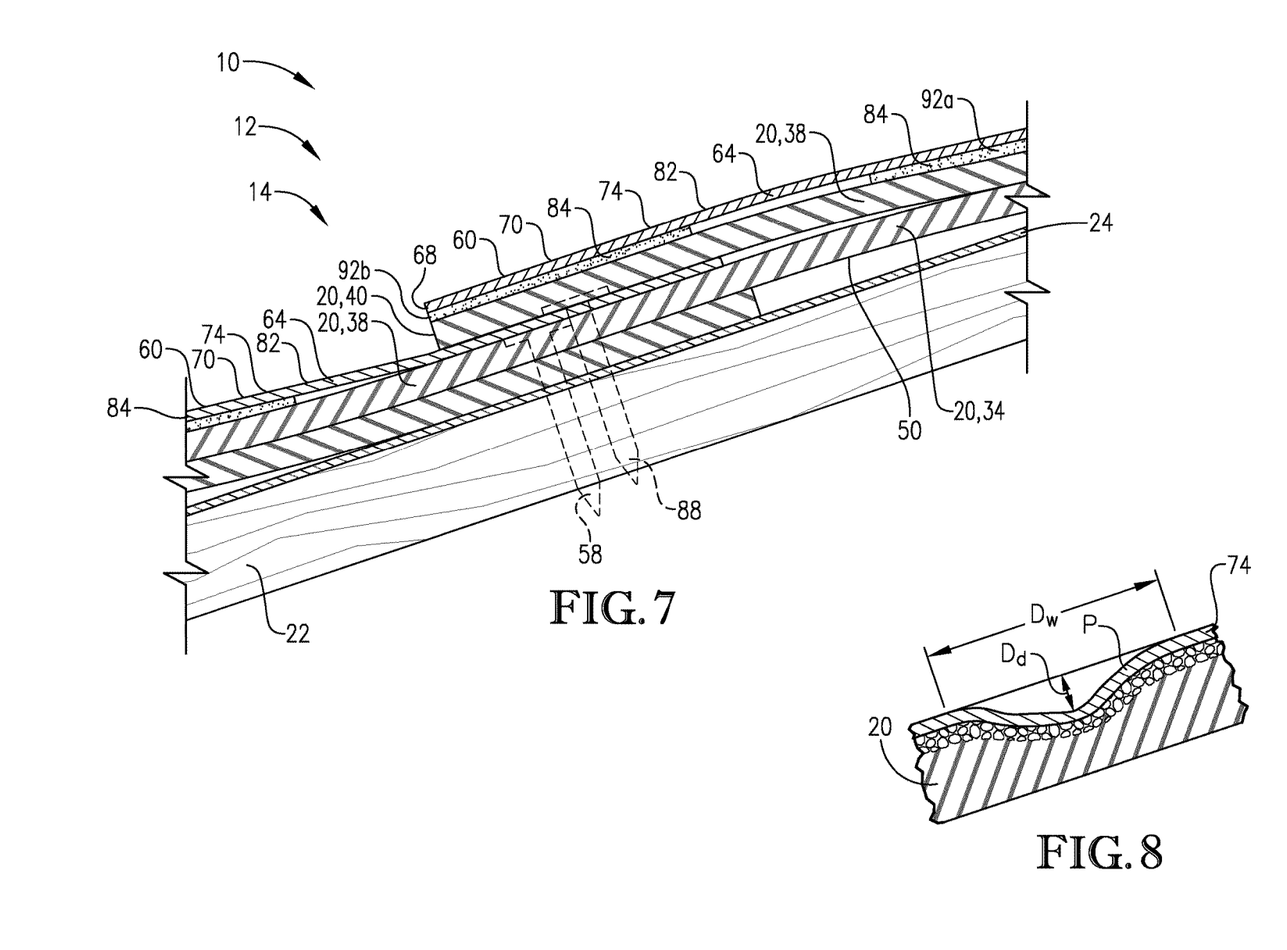
FIG. 7 is an enlarged fragmentary cross section view similar to that shown in FIG. 6, particularly showing the partially overlapped relationship of the panels and the fasteners securing the panels in place.
FIG. 8 is a greatly enlarged fragmentary cross section view of the roof construction shown in FIG. 1, showing the recording panel and underlying shingle in an indented condition, with a dimensionally measurable depression caused by a hail impact.

The shingles are secured to the roof 12 by shingle fasteners 58, preferably comprising nails in the illustrated embodiment (see FIGS. 3, 6, and 7). With reference to the illustrated embodiment, eleven-gauge or twelve-gauge galvanized steel, or a similarly corrosion-resistant, roofing nail will be sufficient for the shingle fastener 58. As illustrated in FIGS. 6 and 7, it is generally preferable for the fasteners 58 to be long enough to extend through the shingles 20, the underlayment 24, and the bottom surface of the roof deck 22 (or penetrate at least three-fourths (3/4) of an inch into the roof deck). However, the present invention is not limited to the to the shingle fasteners 58 of the preferred embodiment. Preferably, the shingle fasteners used and the arrangement thereof on the roof will be compliant with standards set by ASTM International and/or the building codes and standards of the particular jurisdiction wherein the roof construction is located. In the preferred embodiment, the fasteners 58 are spaced along the length of the upper shingle section 34, with preferably four (4) fasteners being provided for each shingle 20. As perhaps best shown in FIGS. 3, 6, and 7, each shingle fastener 58 is positioned essentially at the juncture between the upper and lower shingle sections 34 and 38, such that the fastener 58 extends through the overlapped sections 54 of adjacent courses 28. Further, the adhesive strip 52 is preferably adjacent the shingle fasteners 58 to further facilitate the connection of the overlapped courses 28. Alternative positioning and number of shingle fasteners are within the ambit of the present invention.

Generally, as additional courses 28 of shingles 20 are arranged on the roof 12, the slots 42 of shingles 20 in adjacent courses are staggered (or offset) to reduce the risk of roof leaks. For most applications involving three-tab asphalt shingles, an offset of six (6) inches is sufficient to reduce roof leaks. Alternative or no longitudinal shingle offset is within the ambit of the present invention, but the arrangement of the shingle offset is preferably compliant with standards set by ASTM International and/or the building codes and standards of the particular jurisdiction wherein the roof construction is located.

The recording device 14 is preferably positioned so that one or more hail strikes can be sensed in close proximity to the shingles. Subsequent to a hail storm event, data associated with the hail storm event is preferably retrieved from the recording device 14, as will be discussed in greater detail below.

Figure 2:
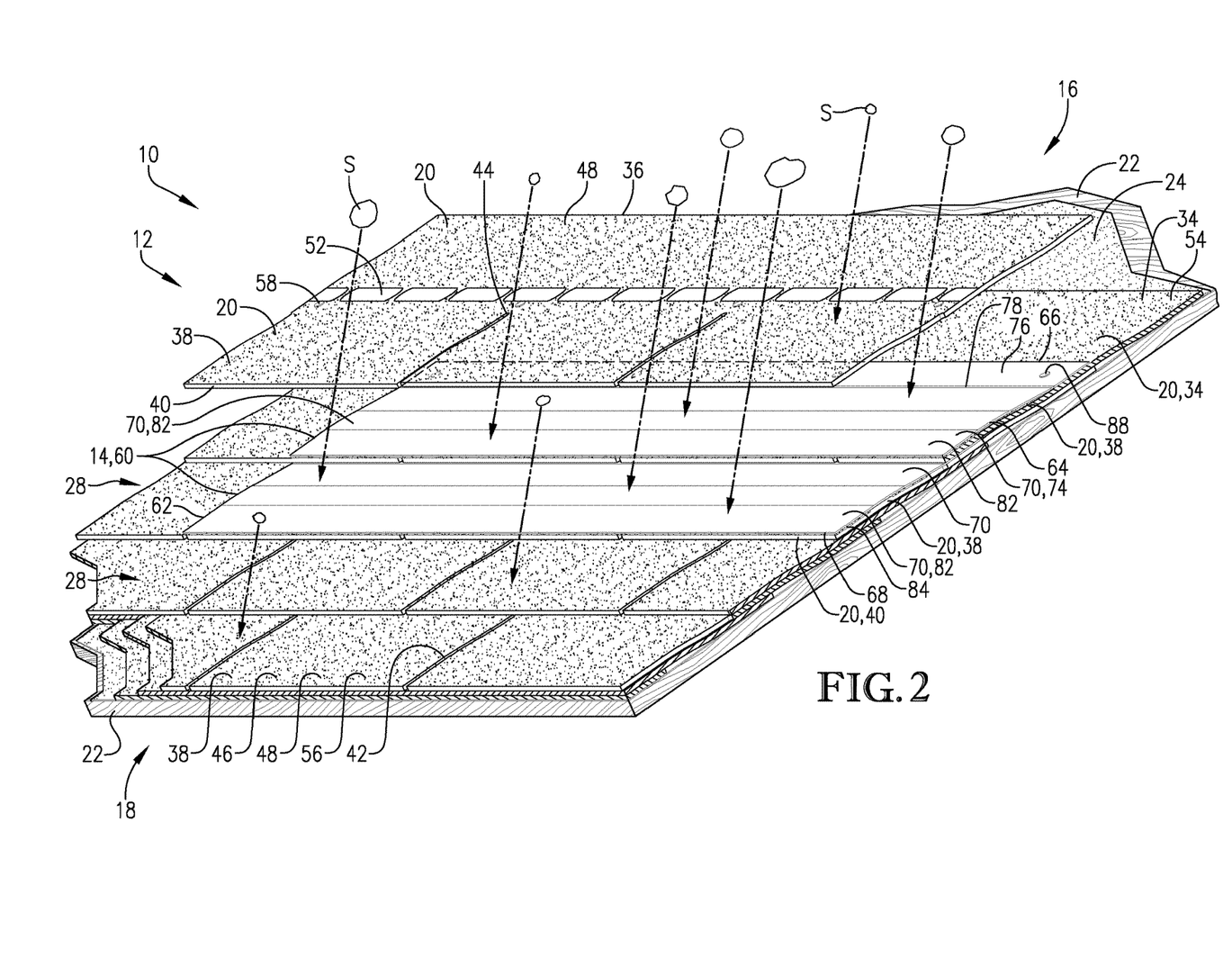
FIG. 2 is an enlarged fragmentary, partially sectioned perspective view of the roof construction shown in FIG. 1 during a hail storm event, with components (or parts thereof) being removed to show the various layers of the roof construction.

The hail strike recording device 14 of the illustrated embodiment includes two (2) low-profile hail strike recording panels 60. As best shown in FIGS. 1 and 2, the recording panels 60 of the illustrated embodiment are arranged in adjacency on the roof, and are in general alignment relative to each other. Although the recording device 14 of the illustrated embodiment includes two (2) recording panels 60, it is within the ambit of the present invention for the roof construction to include only a single recording panel or more than two (2) panels. Additionally, the particular arrangement of the recording panels 60 in the illustrated embodiment should not be construed to limit the scope of the present invention. For example, aspects of the present invention equally apply to roof constructions including multiple spaced apart recording devices, each having one or more panels, aligned or unaligned panels, etc.

Because the recording panels 60 of the illustrated recording device 14 are identically constructed and function in the same way, only one of the panels 60 will be described in detail herein, with the understanding that the other panel includes the same features. However, a recording device including recording panels that are not identical is within the ambit of the present invention.

Figure 4:
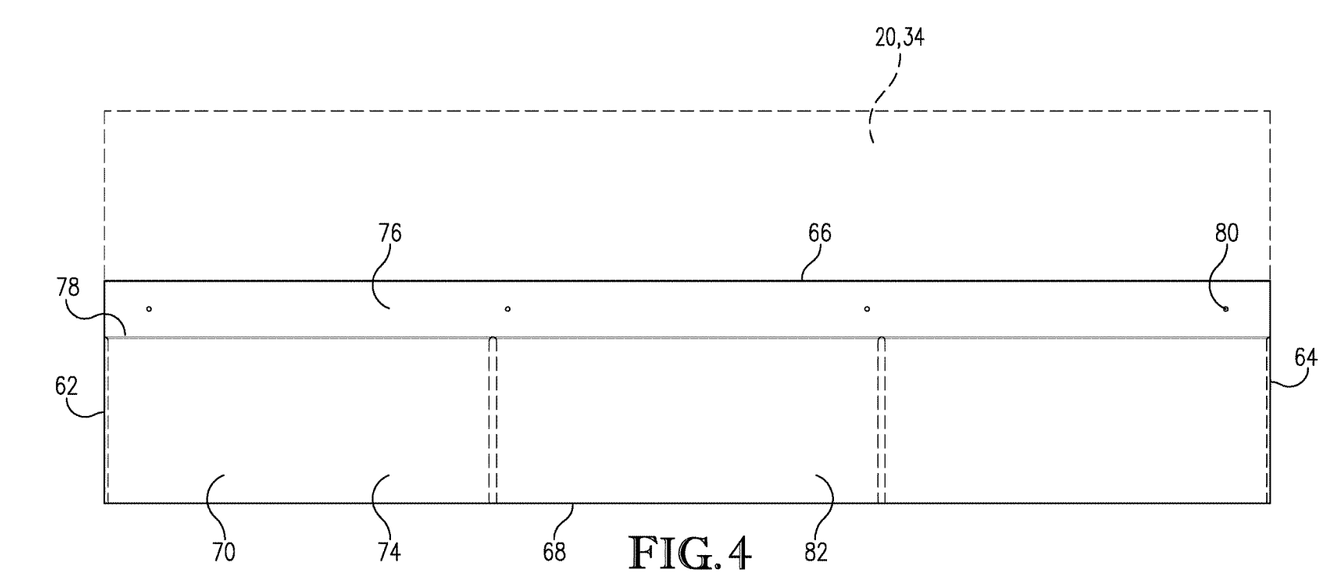
FIG. 4 is a top view of one of the panels, with a corresponding one of the shingles being shown in broken lines.
Figure 5:
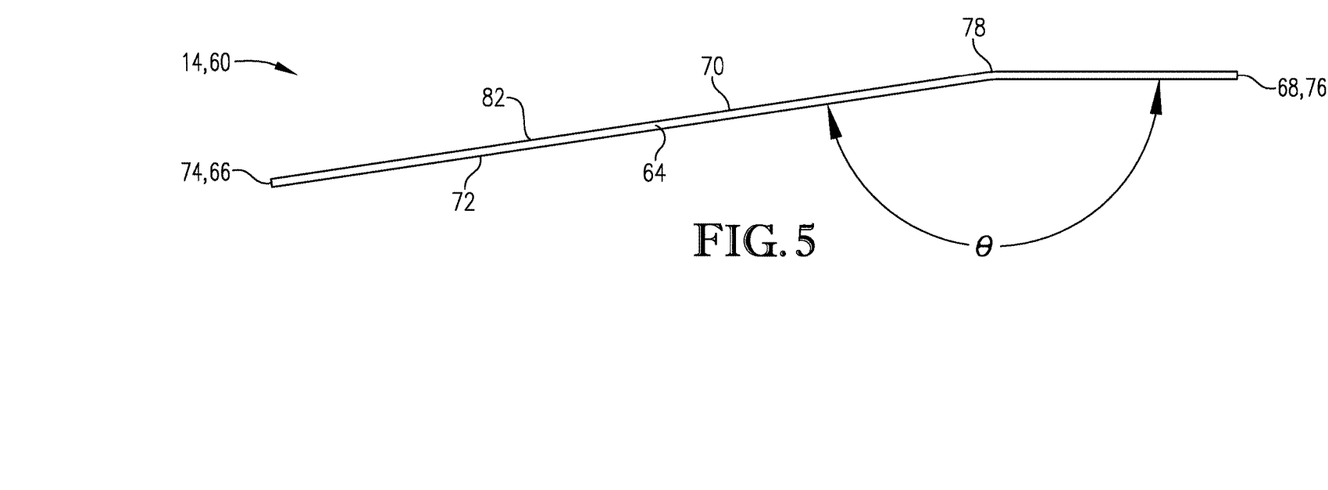
FIG. 5 is side elevation view of the recording panel shown in FIG. 4, particularly showing the angled relationship between the portions of the recording panel.

As perhaps best shown in FIGS. 4 and 5, the low profile recording panel 60 preferably presents a rectangular shape, with opposite ends 62 and 64 and upper and lower sides 66 and 68 extending between the ends 62 and 64. The length of the panel 60 (defined between the ends) preferably coincides with the length of a shingle 20, although the panel width (measured between the sides 66 and 68) is preferably less than the width of the shingle 20. The panel 60 presents opposite top and bottom surfaces 70 and 72, with a panel thickness being defined therebetween preferably in the range of about one hundredth of an inch (0.01") to about five hundredths of an inch (0.05"). Most preferably, the panel 60 has a thickness of about three hundredths of an inch (0.03). For purposes which will be described, the panel 60 is preferably bent to present an impact portion 74 and a mounting portion 76 that are angled relative to one another. More particularly, the panel presents a bend or apex 78 that is preferably parallel to the sides 66 and 68. The impact portion 74 is defined between the lower side 66 and the apex 78, and the mounting portion 76 is defined between the upper side 68 and the apex 78. Spaced along the length of the mounting portion 76 are fastener-receiving openings 80, which will be further described hereinbelow. There are four (4) openings 80 shown in the illustrated embodiment, although an alternative number of openings or altogether different mounting means may be incorporated into the panel without departing from the spirit of the present invention.

Those of ordinary skill in the art will appreciate that the panel 60 may be variously sized and shaped without departing from the spirit of the present invention. For example, the panel need not present a rectangular shape coinciding with that of the shingle. Specifically, the panel may be longer or shorter than the shingle, have an entirely different shape from the shingle, or overlie more than one shingle, without departing from the spirit of the present invention. It will be appreciated, however, that the panel at least partly conform to one or more underlying shingles so as to engage such shingle(s). Therefore, if the shingles have a contoured shape (as opposed to generally planar shape as shown), the panel will be similarly contoured. That is to say, certain aspects of the present invention apply to panels having a concave, convex, or concavo-convex shape to conform to the underlying shingle(s) with which the panel is used.

The low-profile panel 60 is preferably formed from a single sheet of T6061 aluminum. However, the recording panel may be formed of an alternative material, such as an alternative metal and/or synthetic resin material, without departing from the spirit of the present invention. Furthermore, certain aspects of the present invention are equally applicable to an alternative recording panel formed from a different material, two or more materials, laminated dissimilar or similar materials etc.

The impact portion 74 comprises a structure that is preferably deformable and continuous throughout. The impact portion 74 is deformable in response to a hail strike so as to sense a quantifiable characteristic(s) of the hail strike. The top surface 70 of the panel 60 along the impact portion 74 defines an exposed impact surface 82. The preferred impact portion 74 also includes attachment structure 84 which facilitates engagement of the portion 74 to the underlying shingles, which will be discussed in greater detail below.

As will be discussed, the impact portion 74 is preferably calibrated so that deformation caused by a hail strike corresponds with a known impact energy.

The impact portion 74 of the illustrated embodiment is substantially planar prior to installation and initial use. The term "substantially planar" preferably refers to a maximum surface deviation of the impact portion, measured along the direction normal to the exposed impact surface 82, that ranges from about zero (0) inches to about one (1) inch and, more preferably, from about zero (0) inches to about one-quarter (¼) inch. However, for some aspects of the present invention, the impact portion could be configured so that the exposed impact surface has a nonplanar shape (e.g., where the exposed surface of the shingles present a concave, convex, or concavo-convex shape).

The low-profile panel 60 is configured to be installed either during the construction of new roofs or onto existing roof constructions. In the illustrated embodiment, the recording panel 60 is preferably arranged on the roof 12 so that the exposed impact surface 82 faces skyward in generally the same orientation as the exposed surface 56 of the lower shingle section (see FIGS. 1-3). As used herein, "generally the same orientation" preferably means that surfaces exposed surfaces 56 and 82 face the same direction. For example, with the exposed surfaces 56 and 82 the direction normal (i.e., perpendicular) to the exposed impact surface 82 is about the same as the direction normal to the exposed shingle surface 56. Furthermore, this also means that the preferred planar impact portion 74 presents a shape that closely conforms to that of the exposed shingle surface 56.

With the preferred orientation of the recording panel 60, a hail strike on the impact portion 74 is identical (or at least substantially similar) to that which would have been experienced by the roof 12 if the hail had struck the shingles 20 rather than the impact portion 74. This means that hail strikes against the recording panel 60 exert an impact energy that is nearly identical to that which would have been absorbed by the shingles 20 if the hail had struck the shingles 20 instead. That is, there is no meaningful difference (in terms of measuring roof damage) between the impact energy absorbed by the recording panels 60 and the impact energy that would have been absorbed by the shingles 20 if the hail had struck the shingles 20 instead.

Most preferably, the impact portion 74 of the panel 60 not only overlies the exposed shingle surface 56, but it also engages the surface 56. That is to say, the impact portion 74 engages and overlies at least part of the lower section 38 of one or more of the corresponding shingles 20 underlying the impact portion 74 (see FIGS. 2 and 3). As used herein, the phrase "engages and overlies" (or engaging and overlying) refers to the relationship of the recording panel 60 and the underlying shingle(s) 20, wherein at least part of the recording panel 60 substantially covers and contacts the lower portion 38 of one or more of the underlying shingles 20. The engaging and overlying relation of the impact portion 74 and the lower shingle section 38 of the corresponding shingle 20 will be discussed in greater detail below.

Again, the impact portion 74 of the panel 60 is preferably coextensive with the lower section 38 of the underlying shingle 20 (see FIG. 4). As best shown in FIGS. 6 and 7, the lower side 66 of the panel 60 is preferably flush (or in vertical alignment) with the butt end 40 of the corresponding shingle 20. However, it is within the ambit of the present invention for the impact portion 74 not to match the shape and size of the lower shingle section 38. For example, the lower side 66 of the panel 60 and the butt end 40 of the underlying shingle 20 need not be aligned. The impact portion may also overlie and engage only part of one of the shingles or be larger than the lower shingle section to overlie and engage multiple ones of the shingles.

The preferred recording panel 60 also extends upwardly relative to the lower shingle section 38 so that the mounting portion 76 is positioned adjacent to one of the overlapped shingle sections 54. More preferably, the mounting portion 76 is positioned between the overlapped shingle sections 54, such that the mounting portion 76 is positioned above the upper section 34 of the underlying shingle 20 and below the lower section 38 of one or more respective upper shingles 20. Because the illustrated shingles 20 of adjacent courses 28 are longitudinally offset, and the illustrated panel 60 is similar in length and longitudinally aligned with the underlying shingle 20, the illustrated mounting portion 76 is positioned underneath two (2) of the shingles 20 of the superjacent course. Furthermore, with the preferred adjacently positioned pair of panels 60, the mounting portion 76 of the subjacent panel 60 underlies the lower shingle section 38 that is engaged and overlain by the superjacent panel 60 (see FIGS. 5 and 7). Therefore, in the illustrated embodiment, the mounting portion 76 of the lower panel 60 is underneath part of the impact portion 74 of the upper panel 60. However, it should be understood that the present invention equally applies to recording panels wherein the mounting portion is configured to be positioned between the upper section and/or the lower section of any one or more of the other shingles besides the corresponding shingle 20 and the respective upper shingle 20 as depicted in the illustrated embodiment. Furthermore, according to some aspects of the present invention, the mounting portion need not be positioned between the overlapped shingle sections. For example, it is within the ambit of the present invention to secure the mounting portion on the top of the overlapped sections.

In the illustrated embodiment, a plurality of mounting fasteners 88 secure the mounting portion 76, and thereby the panel 60, to the roof 12. The mounting fasteners 88 extend transversely through the mounting portion 76 and the upper section 34 of one or more of the corresponding shingles 20. The illustrated fasteners 88 are depicted as roof nails. Preferably, the mounting fasteners 88 are galvanized steel, or similarly corrosion-resistant, roofing nails. As depicted in FIGS. 6 and 7, the mounting fasteners 88 and the shingle fasteners 58 are slightly offset with the respective heads being overlapped; however, the principles of the present invention are equally applicable to alternative positioning of the fasteners 88 and 58. For example, the mounting portion and the underlying shingle can be simultaneously attached by a common fastener without departing from the spirit of the present invention.

It should be also understood that the present invention is not limited to the mounting fasteners 88 depicted in the illustrated embodiment. For example, alternative means of securing the mounting portion of the recording panel, such as staples and/or adhesive materials, are within the ambit of the present invention. Additionally, it should be understood that the present invention equally applies to recording panels wherein the mounting portion is configured to be secured to the upper section and/or the lower section of any one or more of the other shingles besides the corresponding shingle 20. Furthermore, the present invention equally applies to recording panel configurations having only an impact portion.

The impact portion 74 and the mounting portion 76 preferably define an angle θ therebetween (see FIG. 5). The angled relationship of the portions 74 and 76 facilitates engagement of the impact portion 74 with the lower section 38 of the underlying shingle 20. More particularly, when the mounting portion 76 is secured to the sloped roof 12, the angled relationship causes the impact portion 74 to be urged into contact with the lower section 38 of the underlying shingle(s) 20. More preferably, the recording panel 60 is secured to the roof 12, such that the impact portion 74 is yieldably pressed against the underlying shingle(s) 20. The angled relationship therefore provides resistance to disengaging movement of the impact portion 74. Preferably, the angle θ ranges from about one hundred seventy three degrees (173°) to about one hundred sixty nine degrees (169°) and, more preferably, is about one hundred seventy one degrees (171°). It may be said the impact portion 74 is most preferably angled nine degrees (9°) relative to the mounting portion 74. Alternative angles or no angle are within the ambit of the present invention.

In the illustrated embodiment, panel 60 is arranged so that the apex 78 (defined at the junction of the relatively angled panel portions 74 and 76) is aligned with the lower end 40 of the overlying shingle 20 (see, e.g., FIGS. 2 and 6). Therefore, the mounting portion 76 is preferably concealed between the overlapped sections 54 and the impact portion 74 is preferably exposed, such that hail stones are permitted to directly strike the impact portion 74.

As previously noted, the impact portion 74 includes an attachment structure 84 that facilitates overlapping engagement of the impact portion 74 to the underlying shingle 20. In the illustrated embodiment, the attachment structure 84 comprises an adhesive layer for adhering the impact portion 74 to the lower section 38 of the corresponding shingle 20. As perhaps best shown in FIGS. 3 and 7, the adhesive layer 84 is preferably applied in two (2) substantially uniform sections or beads 92a and 92b. The beads 92a and 92b preferably extend the entire width of the impact portion 74 between the bottom panel surface 72 and the top surface 48 of the underlying shingle 20.

The adhesive beads 92a and 92b are depicted in the illustrated embodiment as uniform rectangles, having a uniform thickness. However, the depicted dimensional uniformity merely serves to generally illustrate the preferred uniform application of the adhesive material. The shape and dimension of the illustrated adhesive material 84 does not limit the present invention. Additionally, the adhesive material may be arranged differently than that shown in the illustrated embodiment without departing from the spirit of the present invention.

Layer 84 is preferably formed of a material compatible with the shingles. In fact, many shingle manufacturers recommend their own adhesive or recommend an approved adhesive. One suitable adhesive material is MasterSeal® NP1—High Performance Polyurethane Sealant (a product manufactured by BASF Corporation). It is also noted that an alternative structure may be used to secure the impact portion to the underlying shingle (e.g., fasteners, welding, combinations of the above, etc.), without departing from the spirit of the present invention. Moreover, the principles of the present invention equally apply to roof constructions wherein the impact portion is secured to the underlying structure.

The illustrated recording panel 60 can be installed as part of a new roof construction or onto an existing roof. That is, the recording panel 60 may be installed during the installation of the shingles or after installation of the shingles is complete. The recording panel 60 could also be attached to the roof at different times. For instance, one or more previously installed recording panels 60 could be replaced with one or more new recording panels 60 (e.g., subsequent to a hail storm event).

Preferably, the recording panel 60, (or at least the exposed portion of the top surface, which is essentially coextensive with the impact portion) is colored (or painted) to substantially match the color of the shingles (not shown). A durable coloring agent/coating capable of withstanding prolonged exposure to the surrounding environment is preferred. It has been found that colored coatings comprising a thermoplastic fluoropolymer provide sufficient durability and aesthetic appeal. One such coating is Kynar®, a polyvinylidene fluoride (PVDF) resin produced by the Arkema Group (see www.kynar.com). It should be understood that other coloring agents/coatings can be used without departing from the spirit of the present invention.

To ensure statistically accurate data pertaining to a hail strike event experienced by the entire roof structure is obtained, the recordable portion of the recording device 14 (which constitutes the combined surface area of the pair of panels 60) preferably presents a minimum impact surface area. The minimum impact surface area is generally proportional to the surface area of the roof wherein damage caused by hail strikes are being evaluated. Preferably, the surface area of the recordable portion of the recording device 14 will cover about one-percent (1%) to about four-percent (4%) of the surface area of the roof whereon damage caused by hail strikes are being evaluated. The present invention is not limited to recording devices presenting the minimum impact surface area, and applies equally to roof constructions wherein the recording device presents an impact surface area different from that discussed above.

It will be appreciated that the desired density of the recording devices 14 can be affected by the roof configuration and the configuration of vertical roof projections. Furthermore, the presence of multiple buildings in a region with installed recording panels could affect the desired density of recording panels (e.g., where the desired density is reduced because one or more adjacent buildings have (or will have) a recording panel installed).

Again, the recording panel 60 serves to record data associated with a hail storm event. The recorded data is in the form of one or more dimensionally measurable depressions (i.e., indentations) P caused by one or more corresponding hail strikes that plastically deform the impact portion 74 along the top surface 70. In particular, each depression P presents a maximum depth dimension Dd and a maximum width dimension Dw (see FIG. 8). The dimensions Dd and Dw of the depressions P each have properties associated with the impact energy of the corresponding hail strike.

The dimensions Dd and Dw can be collected manually using conventional measurement tools. For instance, the depth dimension Dd can be measured with a conventional depth micrometer, and the width dimension Dw can be measured with a conventional ruler or micrometer. These manual measurements can then be recorded manually and/or electronically for later reference.

It is also within the ambit of the present invention where the dimensions Dd and Dw are measured and recorded using alternative devices such as electronic or automated measurement tools. For instance, an electronic scanner can collect one or more images of the indented impact surface 82 and record image data that can be used to digitally re-create the indented surface. In this manner, the dimensions Dd and Dw can be subsequently determined from the recorded image data.

Where the indented panel 60 is removed after the hail storm event (e.g., due to excessive panel damage), the indented panel 60 can be replaced with a new panel.

Using the recorded dimension data from the recording panel 60, an impact energy value can be calculated for a corresponding depression P. Specifically, the depth Dp and width Dw dimensions for each depression P can be used to calculate the corresponding impact energy value of the hail stone S that formed the depression P. This is possible because the hail impact portion 74 of the recording panel 60 is preferably calibrated so that various degrees of deformation caused by hail strikes correspond with known values of impact energy. More specifically, the illustrated impact portion 74 has been calibrated so that recorded depressions P have a measured-dimension corresponding with an empirically generated impact energy. More specifically, each range of depth dimensions corresponds to a range of impact energy values. The following Tables provide corresponding ranges of depression depths and ranges of impact energy. It is noted that the values are limited to hail stones ranging from about one and two-tenths inches (1.2") and about two inches (2"). It has been determined that hail stones smaller than the specified dimensions rarely (if ever) cause damage to acceptably aged roofs, and hail stones larger than the prescribed range cause sufficiently visible roof damage that use of the panel is unnecessary.

TABLE 1

| Depression Depth (inches) | Impact Energy (foot-pounds) |
|---|---|
| 0-0.005 | 0-1 |
| 0.005-0.02 | 1-5 |
| 0.02-0.04 | 5-10 |

TABLE 2

| Depression Depth (inches) | Impact Energy (foot-pounds) |
|---|---|
| 0-0.01 | 0-1 |
| 0.01-0.03 | 1-5 |
| 0.03-0.05 | 5-10 |
| 0.05-0.10 | 10-25 |

The impact energy values identified in Table 1 correspond to a hail strike impacting the impact portion 74 in an area where the impact portion 74 is in direct contact with the underlying shingle 20 (or other underlying roof surface).

The impact energy values identified in Table 2 correspond to a hail strike impacting the impact portion 74 in an area where the impact portion 74 is not in direct contact with the underlying shingle 20 (or other underlying roof surface). For example, the impact portion 74 may not be in direct contact with the corresponding shingles 20 in areas where the impact portion 74 spans one of the slots 42, or where the impact portion 74 spans adjacent shingles projecting skywardly at different extents or angles relative to the roof. This is a so-called "brigaded area."

Thus, for each measured depression depth dimension, a value of impact energy can be calculated from the chart in Table 1 and/or Table 2. It will also be appreciated that the correlation data in Tables 1 and 2 can be used to calculate impact energy for a depth dimension Dd falling within a range of listed depth dimensions Dd. This calculation can be done using conventional techniques, such as by using linear interpolation to determine the impact energy. Also, a non-linear curve fit of the depression depth and impact energy data can be generated and used to determine the impact energy from the curve fit representation of the data.

As will be discussed, the correlation identified in Tables 1 and 2 between depth dimension Dd and impact energy is developed empirically for the illustrated impact portion 74 (or for other recording panels) so as to calibrate the impact portion 74 for recording hail strikes.

In some instances, it might be possible to calculate, from the collected data including information about the depressions P, a mass and maximum diameter dimension of the associated hail stone S from the recorded dimension data.

As mentioned above, the depressions P have depth Dp and width Dw dimensions associated with the impact energy of the corresponding hail strike. This dimension data collected for all of the recorded depressions associated with one of the recording panels can be analyzed to calculate statistical information about the hail strikes. For instance, the dimension data can be analyzed to calculate mean (and/or median) depth and width dimensions for the depressions P, and the standard deviation of depth and width dimensions for the depressions P. The dimension data can also be used to calculate the maximum depth and width dimensions for depressions P.

Furthermore, the dimension data for multiple recording panels 60 can be analyzed collectively to calculate the statistical values mentioned above with respect to all of the multiple recording panels 60. Such calculations can be performed for multiple recording panels 60 installed on a single roof. Alternatively, these calculations can also be performed for multiple recording panels installed on multiple roofs (e.g., recording panels deployed across multiple, spaced apart buildings located on a single real estate property or on multiple properties).

Again, the correlation identified in Tables 1 and 2 between depth dimension Dd and impact energy is developed empirically for the illustrated impact portion 74 so as to calibrate the panel for recording hail strikes. Using a drop test similar to that disclosed in ASTM-D3746, a missile (not shown) with a known weight is dropped onto a sample of the roof construction (not shown) at various heights corresponding to the impact energy values listed in Table 1. More particularly, the missile is dropped onto a sample impact portion that is assembled with a sample roof (overlapped shingles and, if desired, an underlying deck). The depth dimension of the depression associated with each missile drop is then measured, recorded, and associated with the respective impact energy value. However, calibration of the impact portion 74 could be performed by other methods. For instance, various features of the impact portion 74 could be specified and tested using a mathematical model and a theoretical determination of its response to hail strikes. Furthermore, such a determination could be done using a computerized model and simulation of the panel (e.g., by performing a finite element analysis of the impact portion's structural design).

Using the calculated energy values, as described above, it is typically desirable to test how a roof sample responds to the calculated energy values. This is particularly the case for hail strikes involving moderately-sized hail stones, when the full extent of any damage to the roof is hidden or is unclear from visual inspection. Moreover, with older roofs having damage or weak-points caused by prolonged exposure to surrounding environment, it may be difficult to determine whether the hail storm event is responsible for any of the damage.

This test would employ a standard drop test procedure, similar to that disclosed in ASTM-D3746. In particular, a missile with a known weight is dropped onto a roof sample at a height corresponding with a desired value of impact energy. Where the roof construction comprises an intact roof deck that is laid over trusses (or rafters) having sixteen (16) on-center spacing, the roof sample to be tested preferably includes a number of the overlapped shingles 20 taken from the roof 12 immediately adjacent to the impact portion 74. However, if the roof construction comprises a compromised (or rotted) roof deck and/or the roof deck is laid over trusses (or rafters) having an on-center spacing substantially greater than sixteen (16) inches, the roof sample to be tested preferably includes superimposed samples (or portions) of the roof deck, underlayment, and shingles taken from the roof 12 immediately adjacent to the impact portion. Furthermore, the roof sample may include sample portions not taken from the roof construction but substantially identical to the respective roof deck, underlayment, and/or shingles. The drop test of the roof sample is preferably done remotely from the roof construction 10, but could be performed on a sample that remains attached to the roof.

In most instances, the desired impact energy value for this test is the greatest value of impact energy calculated from the corresponding hail strikes. More particularly, in conducting the drop test, the missile is set a height that produces the maximum impact energy as experienced by the panel. The maximum energy should correspond with the depression(s) calibrated to the highest energy levels. It will be appreciated that the drop test may be performed one or more times at each desired height.

Subsequent to the drop test, the sample of the shingles 20 can then be visually inspected for visible structural damage, such as plastic deformation, cracking, and/or tearing.

Importantly, this drop test procedure can also be used to empirically determine a rating for a shingle, underlayment, roof deck, or other roofing material based upon the value of impact energy, associated with a hail strike, that the material sample can withstand without being damaged (e.g., without retaining damage in the form of plastic deformation, cracking, and/or tearing). For instance, the drop test can be performed at a series of impact energy values to determine the minimum value of impact energy required to generate a threshold level of damage that would trigger replacement of the roof. This information may, however, not be useful for aged roofs.

As discussed above, multiple recording devices 14 can be deployed across one or more buildings to sense a hail storm event. It is believed that deployment of multiple recording devices 14 across a wide area can potentially provide a better understanding of properties (such as the physical size, strength, path, speed, and timing) of a hail storm event.

Where the roof construction includes a video camera to record video data of the hail storm event recorded by the panel, this video data can be evaluated and compared to the recorded data from the panel. In particular, the recorded video data can be used to identify an individual hail stone S from the video data and where the hail stone S impacts the impact portion. In this manner, the video data is used to associate the hail stone S with a particular depression P in the impact portion.

With this association, the video data can be used to estimate the maximum diameter dimension of the hail stone S. The estimated maximum diameter dimension of the hail stone S can then be compared to the calculated maximum diameter dimension, e.g., to verify the accuracy of the dimension calculated from the recorded impact data.

In at least some instances, it is anticipated that recorded data from the recording device 14 could be correlated with weather radar data to provide an even more detailed and complete history of the hail storm event. Various types of radar data could be compared and correlated with recorded data from the recording devices 14. For instance, dual polarimetric data could be correlated with the recorded data to interpolate and/or extrapolate properties of the hail storm event, such as hail size, impact energy, etc. at locations spaced from the recording device 14 and/or at times different from times at which hail strikes are recorded by the recording device 14. That is, hail storm properties could be interpolated and/or extrapolated as a function of location and/or time.

The correlation can be used to determine the maximum impact energy from hail and the frequency of large hail stones that could have occurred within a given area (e.g., a two (2) inch diameter hail stone having an impact energy of twenty (20) ft-lb occurred about four (4) times in one hundred (100) square meters, with a ninety five percent (95%) confidence level). It will be appreciated that interpolation and/or extrapolation of data can be performed using conventional mathematical curve fitting techniques, e.g., by using a Gaussian curve fit algorithm. Preferred dual polarimetric factors (or moments) for correlation with recorded data include, for instance, reflectivity, differential reflectivity, correlation coefficient, and specific differential phase.

The recording device 14 of the present invention may also include an identification plate (not shown) that presents identification indicia that is unique to each recording device 14 and, therefore, uniquely identifies the recording panel. Preferably, the indicia is in the visible form of a unique serial number, which could be printed, stamped, or otherwise permanently added to the identification plate. However, the indicia could have other visible forms (such as a scannable bar code) within the scope of the present invention. Yet further, the recording panel could have another element to uniquely identify itself, such as an electronic RFID chip.

In use, the recording device 14 is preferably installed as part of the roof construction 10, as described above. The recording device 14 is used to record information about hail strikes substantially similar to hail strikes experienced by the roof from a hail storm event. Associated with the installation process, the identification indicia of each installed recording panel may be recorded in a manual or electronic database. Other information associated with each recording panel can also be recorded in the database, such as installation date, installer contact information (e.g., installer name, address, and phone number), and specification information for the recording panel. Furthermore, initial ambient data associated with installation can also be recorded to the database, such as sensed load data, pressure data, video image data, still image data, wind velocity and direction data, and temperature data. Those of ordinary skill in the art will appreciate that the illustrated recording device 14 is particularly suitable for use with shingled roofs. Moreover, each panel 60 provides the desired recordation of information while maintaining a low-profile, thereby minimizing any negative impact on the roof aesthetics.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A roof construction comprising:
   a sloped roof including a plurality of shingles arranged in partially overlapped courses,
   each of said shingles presenting upper and lower shingle sections,
   said shingles being arranged such that adjacent Courses present overlapped shingle sections, with the upper section of a lower one of the shingles underlying the lower section of an upper one of the shingles; and
   a hail strike recording panel including a mounting portion and a deformable hail impact portion, with the impact portion being calibrated so that deformation caused by a hail strike corresponds with a known impact energy,
   said panel being secured to the roof so that the impact portion faces skyward in generally the same orientation as the roof,
   said impact portion of the panel engaging and overlying at least part of one or more of the shingles,
   said mounting portion being secured to the roof and positioned between the overlapped shingle sections, such that the mounting portion is above the upper section of a corresponding shingle and below the lower section of one or more of the upper shingles.

2. The roof construction as claimed in claim 1,
   said impact portion of the panel engaging and overlying at least part of the lower section of the corresponding shingle.

3. The roof construction as claimed in claim 1,
   a mounting fastener securing the mounting portion to the roof.

4. The roof construction as claimed in claim 3,
   said mounting fastener extending through the mounting portion and the upper section of the corresponding shingle.

5. The roof construction as claimed in claim 1,
   said impact and mounting portions presenting an obtuse angle therebetween.

6. The roof construction as claimed in claim 5,
   said impact portion including a panel section and an adhesive interposed between the panel section and the lower portion of the corresponding shingle,
   said adhesive adhering the panel section to the lower portion of the corresponding shingle.

7. The roof construction as claimed in claim 6,
   said panel section being formed of an aluminum plate having a thickness of about 0.01 inch to about 0.05 inch.

8. The roof construction as claimed in claim 1,
   said impact and mounting portions presenting an obtuse angle therebetween.

9. The roof construction as claimed in claim 8,
   said angle being between about 169° and about 173°.

10. The roof construction as claimed in claim 8,
    a mounting fastener securing the mounting portion to the roof.

11. The roof construction as claimed in claim 10,
    said mounting fastener extending through the mounting portion and a corresponding one of the shingles.

12. The roof construction as claimed in claim 8,
    said impact portion including a pane section and an adhesive interposed between the panel section and said at least part of one or more of the shingles,
    said adhesive adhering the panel section to said at least part of one or more of the shingles.

13. The roof construction as claimed in claim 1,
    said impact portion being configured so that deformation caused by the hail strike creates a dimensionally measurable depression associated with the known impact energy.

14. The roof construction as claimed in claim 13,
    said panel being formed of an aluminum plate having a thickness of about 0.01 inch to about 0.05 inch.

15. The roof construction as claimed in claim 1,
    a second hail strike recording panel including a second deformable hail impact portion that is calibrated so that deformation caused by a hail strike corresponds with a known impact energy,
    said second panel being secured to the roof so that the second impact portion faces skyward in generally the same orientation as the roof,
    said second impact portion of the panel engaging and overlying at least part of one or more of the shingles.

16. The roof construction as claimed in claim 15,
    each of said shingles presenting upper and lower shingle sections,
    said shingles being arranged such that adjacent courses present overlapped shingle sections, with the upper section of a lower one of the shingles underlying the lower section of an upper one of the shingles, said impact portion of each panel engaging and overlying at least part of the lower portion of a corresponding shingle.

17. The roof construction as claimed in claim 16, said corresponding shingles being in adjacent courses, such that one of the panels is positioned lower than the other panel.

18. The roof construction as claimed in claim 17, each of said panels including a mounting portion adjacent the impact portion, with each mounting portion being positioned between respective overlapped shingle sections, such that each mounting portion is above the upper section of the corresponding shingle and below the lower section of one or more of the respective upper shingles, said mounting portion being secured to the roof.

19. The roof construction as claimed in claim 18, said panels being adjacent one another, such that the mounting portion of said one of the panels is positioned below the lower section of the corresponding shingle for the other panel.

\* \* \* \* \*